(12) United States Patent
Klopotek

(10) Patent No.: US 12,329,632 B2
(45) Date of Patent: Jun. 17, 2025

(54) LENTICULES FOR INTRASTROMAL CORNEAL IMPLANTATION

(71) Applicant: Gebauer-Klopotek Patent Verwaltungs—UG, Neuhausen (DE)

(72) Inventor: Peter J. Klopotek, Neuhausen (DE)

(73) Assignee: Gebauer-Klopotek Patent Verw Altungs-UG, Neuhausen (DE)

( * ) Notice: Subject to any disclaimer, the term of this patent is extended or adjusted under 35 U.S.C. 154(b) by 0 days.

(21) Appl. No.: 18/504,370

(22) Filed: Nov. 8, 2023

(65) Prior Publication Data

US 2024/0065826 A1 Feb. 29, 2024

Related U.S. Application Data

(62) Division of application No. 16/330,080, filed as application No. PCT/IB2017/055505 on Sep. 12, 2017, now abandoned.

(60) Provisional application No. 62/393,448, filed on Sep. 12, 2016.

(51) Int. Cl.
| | |
|---|---|
| A61F 2/14 | (2006.01) |
| A61F 9/007 | (2006.01) |
| A61K 35/12 | (2015.01) |
| A61K 35/30 | (2015.01) |
| A61L 27/36 | (2006.01) |

(52) U.S. Cl.
CPC .............. *A61F 2/142* (2013.01); *A61F 9/007* (2013.01); *A61K 35/12* (2013.01); *A61K 35/30* (2013.01); *A61L 27/3633* (2013.01); *A61L 27/3641* (2013.01); *A61L 27/3687* (2013.01); *A61L 2430/16* (2013.01)

(58) Field of Classification Search
None
See application file for complete search history.

(56) References Cited

U.S. PATENT DOCUMENTS

| | | |
|---|---|---|
| 4,676,790 A | 6/1987 | Kern |
| 4,793,344 A | 12/1988 | Cumming et al. |
| 5,288,436 A | 2/1994 | Liu et al. |
| 6,110,166 A | 8/2000 | Juhasz |
| 2007/0142908 A1 | 6/2007 | Xu |
| 2010/0036488 A1 | 2/2010 | Juan, Jr. et al. |
| 2010/0215717 A1 | 8/2010 | Soker et al. |
| 2011/0183404 A1 | 7/2011 | Wee et al. |
| 2012/0010728 A1 | 1/2012 | Sun et al. |
| 2012/0310223 A1 | 12/2012 | Knox et al. |
| 2015/0126453 A1 | 5/2015 | Xu et al. |
| 2017/0119928 A1 | 5/2017 | Rzany et al. |
| 2018/0228599 A1 | 8/2018 | Elisseeff et al. |
| 2019/0240003 A1 | 8/2019 | Klopotek |
| 2019/0307551 A1 | 10/2019 | Peyman |
| 2020/0000965 A1 | 1/2020 | Klopotek |
| 2020/0146812 A1 | 5/2020 | Klopotek |
| 2021/0113737 A1 | 4/2021 | Klopotek |

FOREIGN PATENT DOCUMENTS

| | | |
|---|---|---|
| CN | 107233143 A | 10/2017 |
| EP | 2138181 A1 | 12/2009 |
| EP | 2752192 A1 | 7/2014 |
| EP | 3509541 B1 | 9/2021 |
| KR | 20160140493 A | 12/2016 |
| WO | 2002006883 A2 | 1/2002 |
| WO | 2013081943 A1 | 6/2013 |
| WO | 2015010119 A2 | 1/2015 |
| WO | 2015188664 A1 | 12/2015 |
| WO | 2016054793 A1 | 4/2016 |
| WO | PCTIB2016054793 | 8/2016 |
| WO | 2016178586 A2 | 11/2016 |

(Continued)

OTHER PUBLICATIONS

International Invitation to Pay Additional Fees and Partial Search Report for International Application No. PCT/IB2019/000779 dated Jan. 27, 2020.
International Preliminary Report on Patentability, PCT/IB2019/000779, dated Jan. 14, 2021, 11 Pages.
International Search Report and Written Opinion for International Application PCT/IB2019/000779 dated Mar. 20, 2020, 18 pages.

(Continued)

*Primary Examiner* — Javier G Blanco
(74) *Attorney, Agent, or Firm* — Potomac Law Group, PLLC; Reza Mollaaghababa

(57) ABSTRACT

Decellularized and shaped corneal tissue lenticules from allograft and/or xenograft sources and methods of obtaining such lenticules are disclosed. The lenticules are particularly useful as intrastromal lenticular implants in keratoplasty procedures, in which a hinged flap is formed in a patient's cornea and folded back along its hinge to expose the stromal bed of the cornea. The shaped lenticule is then applied to the stromal bed and the flap returned to its original position yielding a new curvature for the cornea and resulting in a desired refractive correction. Fine-tuning of the new refractive power can be achieved by laser ablation either at the same time as implantation or at later time in the event of regression or tonus changes. Methods of decellularizing cornea tissue are disclosed to reduce potential immunogenic reactions on the part of the patient to the implanted lenticule. The lenticules can be further treated to remove immunogenic epitopes. In addition, the posterior and/or anterior surfaces of the lenticule can be treated to assist in intrastromal seating of the lenticule and/or to reduce the likelihood of dislodgement. The methods of forming lenticules can further include preserving at least a portion of the Bowman's membrane. The smoothness of the Bowman's membrane surface also makes it less likely that reopening the flap will dislodge the lenticule.

14 Claims, No Drawings

(56) References Cited

FOREIGN PATENT DOCUMENTS

| WO | 2018029509 A1 | 2/2018 |
| WO | 2018047151 A1 | 3/2018 |
| WO | 2018219045 A1 | 12/2018 |
| WO | 2020008258 A2 | 1/2020 |
| WO | 2021130276 A1 | 7/2021 |

OTHER PUBLICATIONS

International Search Report and Written Opinion, PCT/EP2020/087710, Dated Apr. 13, 2021, pp. 9.

International Search Report and Written Opinion, PCT/IB2017/055505, Dated Jul. 11, 2018, pp. 12.

International Search Report and Written Opinion, PCT/IB2019/000779, Dated Mar. 20, 2020, pp. 14.

Morishige, N., et al., "Three-dimensional analysis of collagen lamellae in the anterior stroma of the human cornea visualized by second harmonic generation imaging microscopy," Investigative Ophthalmology & Visual Science, vol. 52(2): 911-915 (2011).

Patel, S., et al., "Refractive index of the human corneal epithelium and stroma," Journal of Refractive Surgery, vol. 11 (2): 100-105(1995).

Wilson, S.L., et al. 2016 Current Eye Research 41 (6): 769-782. (Year: 2016).

WO 2018219045 translated copy, powered by EPO and Google (17 pages). (Year: 2018).

Written Opinion for International Application PCT/IB2017/055505 dated on Dec. 15, 2017.

Chae, "Investigation of Biomaterials-Based Strategies for Corneal Reconstruction", pp. 1-168, 2016.

U.S. Non-Final Office Action for U.S. Appl. No. 16/728,941 dated Oct. 10, 2024.

Cheng et al., "A structural model for the in vivo human cornea including collagen-swelling interaction", J.R. Soc. Interface, 2015.

Dahl et al., "Corneal collagen cross-linking: An introduction and literature review" Optometry, 2012, vol. 83, pp. 33-42.

Machine translation of CN 107233143, 2024, 8 pages.

Moshirfar et al., "Small-incision lenticule extraction", J Cataract Refract Surg, vol. 41, Mar. 2015.

O'Brart., "Corneal collagen cross-linking: A review", Journal of Optometry, 2014 7, 113-124.

LENTICULES FOR INTRASTROMAL CORNEAL IMPLANTATION

CROSS-REFERENCE TO RELATED APPLICATIONS

This application is a divisional of U.S. patent application Ser. No. 16/330,080 filed Mar. 2, 2019, which is a U.S. national stage filing under 35 U.S.C. § 371 of International Application No. PCT/IB2017/055505 filed Sep. 12, 2017, which claims priority to and the benefit of U.S. Provisional Patent Application No. 62/393,448 filed Sep. 12, 2016, all of which are hereby incorporated herein by reference in their entireties.

BACKGROUND OF THE INVENTION

Vision disorders caused by abnormal refractive conditions, e.g. ammetropia, can be a significant problem for patients of all ages and can often be treated with subtractive laser ablation procedures or keratoplasty. Recently, additive techniques have been developed which can be used in conjunction with subtractive (ablative) techniques. Additive techniques typically involve the transplantation of a lenticule into a patient's cornea after a flap has been cut and folded back to expose an intrastromal region of the cornea. The shape of the lenticule modifies the optical power of the patient's cornea by changing its curvature. The flap can then be replaced on top of the lenticule. A few weeks later, if a change in the tonus of eye occurs, the patient can be assessed and a second step performed, which involves re-lifting the flap and performing refractive ablation of the lenticule with a laser.

However, several problems limit wider acceptance of additive (lenticular) techniques. First, the availability of donor human corneas to form lenticules is quite limited. Additionally, the lenticules, themselves, are difficult to manipulate and prone to movement, especially if the flap must be re-lifted to perform a subsequent ablative procedure. Finally, the long-term transplant rejection rate over a 10-year period can be as high as 10%-20%.

SUMMARY OF THE INVENTION

Decellularized and shaped corneal tissue lenticules from allograft and/or xenograft sources and methods of obtaining such lenticules are disclosed. The lenticules are particularly useful as intrastromal lenticular implants in keratoplasty procedures, in which a hinged flap is formed in a patient's cornea and folded back along its hinge to expose the stromal bed of the cornea. The shaped lenticule is then applied to the stromal bed and the flap returned to its original position imparting a new curvature to the cornea and resulting in a desired refractive correction. Fine-tuning of the new refractive power can be achieved by laser ablation either at the same time as implantation or at later time in the event of regression or tonus changes.

In one aspect of the invention, decellularized corneal lenticules and methods of decellularizing cornea tissue are disclosed to reduce potential immunogenic reactions on the part of the patient to the implanted lenticule. Only about 2 percent of the typical cornea is composed of cells. The other 98 percent is largely extracellular matrix (ECM), primarily collagen, and water. In one preferred embodiment, the cellular component of the lenticule is removed by treatment with a surfactant, such as for example, sodium tetradecyl sulfate (STS), or by enzymatic desolubilization. If desired, additional steps can be taken to further reduce the immunogenicity of the lenticule, especially if the donor source is non-human (xenographic). For example, two non-human epitopes that may be present in xenograph tissue are neu5GC and Alpha-Gal. These undesirable epitopes are present not only inside or on surface of intrastomal cells; a small fraction of the epitopes can be embedded inside the glyco-amino-glycans (GAGs), also known as mucopolysaccharides, that wrap around ECM collagen fibrils. These epitopes can be removed by kinase treatments and additional washing.

The decellularized lenticules of the present invention typically have 60%-100% of cellular materials removed. Preferably, the lenticules are 65%-95% cell-free. Without reciting every possible sub-range between 60% and 100%, it should be clear that all such sub-ranges are contemplated and considered part of the invention. For example, the lenticules can be 60% to 95%, 70% to 100% or 75% to 95% free of cellular materials.

In another aspect of the invention, disc-shaped lenticules according to the invention are obtained by cutting a disc-shaped tissue segment from donor cornea in a manner that preserves the outermost (anterior) surface of the corneal tissue, commonly referred to in human eyes as Bowman's membrane. The tissue segment can be sliced and/or further shaped or cut in such a manner that the desired shape is obtained during the slicing procedure. Cutting can be performed mechanically, e.g., with a microkeratome or the like, by laser processing, e.g., or by photo-cleavage with a femtosecond laser. To reduce the possibility of asymmetry, the tissue segment is preferably taken from the central portion of the donor cornea, e.g., with the optical or geometric axis of the donor cornea preserved at the center of the lenticule. The shape of tissue segment will be dictated by the dioptic power change needed to correct the patient's refractive error. For example, for correction of hyperopia (hypermetropia) and/or presbyopia, the goal is typically to increase the curvature of the cornea and the desired lenticule shape will be slightly convex on at least one side. Typically, the maximum thickness of the lenticule will be less than 200 micrometers, or in many instances less than 100 micrometers. In special applications the thickness of the lenticule may grow up to 350 micrometers. These cases encompass relatively rare very high hyperopia (which is almost always associated with astigmatism) and keratoconus. In case of keratoconus the lenticule may have a disk-like shape with small or irregular refractive value. The significant purpose of such lenticule is to stabilize the degenerative cornea. Additionally, the surgical/procedural details of such cases may differ from the described standard procedure. In non-standard interventions, practitioners may employ a custom shaped lenticule into surgical procedures involving pocket-forming, sowing, gluing or crosslinking of at least some parts of the cornea.

Importantly, by preserving the top stromal surface, the anterior surface of the lenticule will exhibit a different texture than the other (posterior) surface because this naturally anterior segment of the cornea is denser and smoother due to natural condensation of the outermost layers of stromal tissue. The posterior surface (opposite to anterior surface or Bowman's membrane) will be rougher due to lesser stromal tissue density and the fact that it is formed by mechanical or laser cutting of the tissue. This difference in roughness can be especially advantageous when the lenticule is used for intrastromal implantation because it is highly desirable that the lenticule be strongly adherent to the stromal bed. If a less than optimal refractive result is observed post procedure, the flap may need to be folded back again to permit further keratoplasty (re-sculpting of the lenticule) by laser ablation or the like. Any movement of the lenticule from its original position in the stromal bed could compromise the effectiveness of this keratoplasty. Moreover, the smoothness of the Bowman's membrane surface of the lenticule also makes it less likely that reopening the flap will dislodge the lenticule.

In yet another aspect of the invention, the posterior surface (opposite to the Bowman's membrane) can be treated following excision, shaping and decellularization to make the surface more adherent to the stromal bed. For example, a crosslinking agent can be applied, prior to sterilization and packaging. Alternatively, the adherence-enhancing agent can be applied by the clinician during the procedure before implantation. The anterior surface (the surface with the Bowman's membrane) can be treated to make it less adherent to the flap

DETAILED DESCRIPTION

This invention is not limited to the particular processes, compositions, or methodologies described, as these may vary. The terminology used in the description is for the purpose of describing the particular versions or embodiments only, and is not intended to limit the scope of the present invention. Unless defined otherwise, all technical and scientific terms used herein have the same meanings as commonly understood by one of ordinary skill in the art. All publications mentioned herein are incorporated by reference in their entirety. Nothing herein is to be construed as an admission that the invention is not entitled to antedate such disclosure by virtue of prior invention.

The term "biological sample" refers to tissue, cells, cellular extract, homogenized tissue extract, or a mixture of one or more cellular products. The biological sample can be used or presented in a suitable physiologically acceptable carrier.

As used herein and in the appended claims, the singular forms "a," "an," and "the" include plural reference unless the context clearly dictates otherwise. Thus, for example, reference to a "cell" is a reference to one or more cells and equivalents thereof known to those skilled in the art, and so forth.

As used herein, the term "about" means plus or minus 10% of the numerical value of the number with which it is being used. Therefore, about 100 µm means in the range of 90 µm-110 µm.

The terms "animal," "patient," or "subject" as used herein includes, but is not limited to, humans and non-human vertebrates such as wild, domestic and farm animals. The terms "animal," "patient," or "subject" also refers to the recipient of a corneal lenticule transplant.

The term "xenographic" refers to tissue collected from animals for donation, including pigs (porcine), bovine, apes, monkeys, baboons, other primates, and any other non-human animals.

Generally speaking, the term "tissue" refers to any aggregation of similarly specialized cells which are united in the performance of a particular function.

The term "lenticule" refers to a decellularized, processed donor corneal tissue ready for implantation into a recipient's stromal bed.

This disclosure relates to a decellularized corneal lenticule from allograft and/or xenograft sources and methods of forming a lenticule from donor corneal tissue. The disclosed decellularized corneal lenticules are intended to be used to correct abnormal refractive conditions, such as myopia, hyperopia, presbyopia, and astigmatism.

The cornea can be generally considered to be comprised of 5 layers, from anterior to posterior: the corneal epithelium, a thin but dense top stromal layer (typically referred to as Bowman's membrane in human eyes), the corneal stroma proper, Descemet's membrane, and corneal endothelium. The corneal epithelium is composed of about 6 layers of non-keratinized stratified squamous epithelium cells, which are fast growing and easily regenerated. The anterior stromal layer (e.g., Bowman's membrane) is a tough layer composed mostly of randomly organized, tightly woven collagen type I fibrils. The corneal stroma is a thick, transparent layer consisting of collagen type I fibers arranged in parallel layers. The Descemet's membrane is a thin acellular layer that serves as the basement membrane of the corneal endothelium and composed of less rigid collagen type IV fibrils. Finally, the corneal endothelium is composed of simple squamous or low cuboidal monolayer of mitochondria-rich cells.

As used here, the term "Bowman's membrane" is used to describe the anterior stromal region of any cornea from either human or a donor animal cornea. Although the densified stratum of the human cornea can be more pronounced (and, hence, known as Bowman's membrane in human corneas), all corneas exhibit higher anterior densification and smoothness (relative to stromal bed tissue) to some degree depending on animal species and age. Hence, "Bowman's membrane" is a term used throughout the present application to describe this anterior segment.

As such, the harvesting and processing of donor corneas and the production of lenticules is a crucial element to correction of refractive errors in vision. The lenticules are particularly useful as lenticular implants in keratoplasty procedures, in which a hinged flap is formed in a patient's cornea and folded back along its hinge to expose the stromal bed of the cornea. The shaped lenticule is then applied to the stromal bed and the flap returned to its original position yielding a new curvature to the cornea and resulting in a desired refractive correction. Fine tuning of the new refractive power can be achieved by laser ablation either at the same time as implantation or at later time in the event of regression or tonus changes.

In certain embodiments of the invention, a decellularized corneal lenticule is comprised of a lenticular body derived from donor corneal tissue having an anterior surface that includes at least a portion of top layer from the donor corneal tissue and a posterior surface that is formed to provide the lenticule with a desired shape; and wherein the donor corneal tissue is decellularized.

In certain embodiments, the donor corneal tissue is harvested and decellularized producing lenticules with a reduction in any potential immunogenic reaction on the part of the patient. Only about 2 percent of the typical cornea is composed of cells. The other 98 percent is largely extracellular matrix (ECM), primarily collagen, and water. The decellularized lenticules of the present invention typically have 60%-100% of cellular materials removed. Preferably, the lenticules are 65%-95% cell-free. Without reciting every possible sub-range between 60% and 100%, it should be clear that all such sub-ranges are contemplated and considered part of the invention. For example, the lenticules can be 60% to 95%, 70% to 100% or 75% to 95% free of cellular materials. Decellularization, i.e. the removal of cellular material from the donor corneal tissue, can be accomplished using a variety of techniques. In one preferred embodiment, the cellular material of the cornea is removed by treatment with a chemical. The chemicals used to lyze and remove cells from the cornea include surfactants, such as, sodium tetradecyl sulfate (STS), acids, alkaline treatments, ionic detergents, such as sodium dodecyl sulfate (SDS), non-ionic detergents, such as, Triton X-100, and zwitterionic detergents. In some embodiments, the cellular material of the cornea is removed using an enzymatic treatment. Lipases, thermolysin, galactosidase, nucleases, trypsin, endonucleases and exonucleases are used to remove the cellular material from the cornea. In some embodiments, the cellular material of the cornea is removed using physical techniques. These physical techniques include methods used to lyse, kill, and remove cells from the matrix of a tissue through the use of temperature, force and pressure, and electrical disruption. Temperature methods are often used in a rapid freeze-thaw mechanism. Temperature methods conserve the physical structure of the ECM scaffold. Pressure decellularization involves the controlled use of hydrostatic pressure at high temperatures to avoid unmonitored ice crystal formation that could damage the scaffold. Electrical disruption of the plasma membrane is another option to lyse the cellular material in the cornea.

In embodiments described herein, the lenticule can exhibit even lower immunoreactivity due to the degradation of immunogenic epitopes. This can be an important step when using xenographic donations. For example, two non-human epitopes that may be present in xenograph tissue are N-Glycolylneuraminic acid (neu5GC) and Galactose-alpha-1,3-galactose (Alpha-Gal). These undesirable epitopes are present not only inside or on the surface of intrastomal cells; a small fraction of the epitopes can be embedded in the glyco-amino-glycans (GAGs), also known as mucopolysaccharides, that wrap around ECM collagen fibrils. In certain embodiments, the epitopes are removed by enzymatic treatments, such as kinase treatments, and additional washing. Alternatively, corneal tissue may be harvested from knock-out transgenic animals (e.g., transgenic pigs), which lack any immunogenic epitopes, thus producing non-immunoreactive lenticules without requiring a degradation step.

In embodiments described herein, the decellularized lenticule can be further sterilized in conjunction with packaging and sealing. Sterilization can be accomplished using wet agents, gamma radiation, or electron beams. In one preferred embodiment, sterilization of the decellularized lenticule is performed using electron beams, as damage to the collagen scaffold is less likely to occur.

In another aspect of the invention, the shape and orientation of the lenticule are designed for optimal results. The lenticules according to the invention are obtained by cutting a disc-shaped tissue segment from donor cornea in a manner that preserves the Bowman's membrane as the anterior surface of the lenticule. In some embodiments, the diameter of the lenticule is from about 0.5 millimeters (mm) to about 10 mm from about 3 mm to about 9 mm, from about 4 mm to about 8 mm, or from about 5 mm to about 7 mm. Again, without reciting every possible sub-range between 0.5 mm and 10 mm, it should be clear that all such sub-ranges are contemplated and considered part of the invention The corneal tissue segment can be sliced and/or further shaped to obtain the desired shape. Cutting can be performed mechanically, e.g., with a microkeratome or the like, or by laser processing, e.g., by photo-ablation with an excimer laser or photo-cleavage with a femtosecond laser. To reduce the possibility of asymmetry, the corneal tissue segment is preferably taken from the central portion of the donor cornea, e.g., with the optical or geometric axis of the donor cornea preserved at the center of the lenticule. The shape of corneal tissue segment will be dictated by the dioptic power change needed to correct the patient's refractive error. For example, for correction of hyperopia (hypermetropia) and/or presbyopia, the goal is typically to increase the curvature of the cornea and the desired lenticule shape will be slightly convex on at least one side. In some embodiments, the maximum thickness of the lenticule will be less than 350 micrometers, less than 200 micrometers, or less than or about 100 micrometers. The smaller the diameter and the thinner the lenticule, the faster it will be integrated into the patient's stromal bed.

Importantly, by preserving the Bowman's membrane at the anterior surface of the lenticule, it will exhibit a different texture than the posterior surface because Bowman's membrane is denser and smoother due to the tightly woven collagen type I fibrils. The posterior surface (opposite Bowman's membrane) will be rougher due to a less dense composition of ECM and the fact that it is formed by mechanical or laser cutting of the tissue. This difference in roughness can be especially advantageous when the lenticule is used for intrastromal implantation because it is highly desirable that the lenticule be strongly adherent to the stromal bed. If a less than optimal refractive result is observed post procedure, the flap may need to be folded back again to permit further keratoplasty (re-sculpting of the lenticule) by laser ablation or the like. Any movement of the lenticule from its original position in the stromal bed could compromise the effectiveness of this keratoplasty. Moreover, the smoothness of the anterior surface of the lenticule also makes it less likely that reopening the flap will dislodge the lenticule.

In yet another aspect of the invention, the posterior surface (opposite to the Bowman's membrane) can be treated following excision, shaping and decellularization to make the surface more adherent to the stromal bed. For example, a crosslinking agent or adherence-enhancing can be applied, prior to sterilization and packaging. Alternatively, the crosslinking or adherence-enhancing agent can be applied by the clinician during the procedure before implantation.

In some embodiments, the harvested, shaped and decellularized lenticule will be marked in such a way that the clinician can maintain the proper orientation of the lenticule during the reopening of the flap and laser re-sculpting adjustments. The marking can be accomplished in a variety of ways, but in all instances will be invisible to the patient once the lenticule is in place in the stromal bed. In some embodiments, the marking can be a micropscopic notch in the top anterior portion or the bottom anterior portion of the lenticule. In some embodiments, the marking can be a line or dot made with a dye placed at the top anterior or bottom anterior of the lenticule.

Also disclosed herein are methods of forming a lenticule from donor corneal tissue. In some embodiments, a method of forming a lenticule from donor corneal tissue comprises removing a portion of tissue from a central region of a donor corneal tissue and preserving at least a portion of Bowman's membrane of the donor corneal tissue as an anterior surface of the lenticule; and shaping a posterior surface of said donor corneal tissue to provide a lenticule body of a desired shape. To reduce the possibility of asymmetry, the tissue segment is preferably taken from the central portion of the donor cornea, e.g., with the optical or geometric axis of the donor cornea preserved at the center of the lenticule. The shape of tissue segment will be dictated by the dioptic power change needed to correct the patient's refractive error. For example, for correction of hyperopia (hypermetropia) and/or presbyopia, the goal is typically to increase the curvature of the cornea and the desired lenticule shape will be slightly convex on at least one side. In some special instances, the refractive shape is of lesser importance and stabilization of a degenerative cornea is the main objective of the transplanted lenticule. The thickness of such lenticules may reach in some cases 350 micrometers. These special instances can employ customized lenticule shapes.

In embodiments described herein, the methods produce a lenticule with a shape and density designed for optimal results. The lenticules are obtained by first cutting a disc-shaped tissue segment from donor corneal tissue in a manner that preserves the Bowman's membrane as the anterior surface. In some embodiments, the diameter of the lenticule is from about 0.5 mm to about 10 mm, from about 3 mm to about 9 mm, from about 4 mm to about 8 mm and from about 5 mm to about 7 mm. The tissue segment can be sliced and/or further shaped or cut in such a manner that the desired shape is obtained during the slicing procedure. Cutting can be performed mechanically, e.g., with a microkeratome or the like, by laser processing, e.g., by photo-cleavage with a femtosecond laser. Cutting may be performed, for example, with instruments such those disclosed in International Patent Application No. PCT/IP2016/054793, entitled "Surgical Apparatus and Blade Elements for slicing Lamellar Segments From Biological Tissue," herein incorporated in its entirety by reference.

Lenticules can also be obtained by femtosecond laser ablation. If preservation of the anterior segment is not necessary, lenticules can also be obtained by Small Incision Lenticule Extraction (SMILE) techniques, disclosed for example in U.S. Pat. No. 6,110,166 entitle "Method For Corneal Laser Surgery," also herein incorporated in its entirety by reference.

In embodiments described herein, the maximum thickness of the lenticule will be less than 200 micrometers, less than 100 micrometers, or about 100 micrometers. The smaller the diameter and the thinner the lenticule, the faster it will be integrated into the patient's stromal bed.

The methods used herein preserve the Bowman's membrane at the anterior surface of the lenticule, which exhibits a different texture than the posterior surface because Bowman's membrane is denser and smoother due to the tightly woven collagen type I fibrils. The posterior surface (opposite Bowman's membrane) will be rougher due to a less dense composition of ECM and the fact that it is formed by mechanical or laser cutting of the tissue. This difference in roughness can be especially advantageous when the lenticule is used for intrastromal implantation because it is highly desirable that the lenticule be strongly adherent to the stromal bed. If a less than optimal refractive result is observed post procedure, the flap may need to be folded back again to permit further keratoplasty (re-sculpting of the lenticule) by laser ablation or the like. Any movement of the lenticule from its original position in the stromal bed could comprise the effectiveness of this keratoplasty. Moreover, the smoothness of the anterior surface of the lenticule also makes it less likely that reopening the flap will dislodge the lenticule.

In certain embodiments, the donor corneal tissue is harvested and decellularized producing lenticules with a reduction in any potential immunogenic reaction on the part of the patient. Only about 2 percent of the typical cornea is composed of cells. The other 98 percent is largely extracellular matrix (ECM), primarily collagen and water. The decellularized lenticules produced using the methods of the present invention typically have 60%-100% of cellular materials removed. Preferably, the lenticules are 65%-95% cell-free. Without reciting every possible sub-range between 60% and 100%, it should be clear that all such sub-ranges are contemplated and considered part of the invention. For example, the lenticules produced can be 60% to 95%, 70% to 100% or 75% to 95% free of cellular materials.

In some embodiments, the removal of all or most cellular material from the donor corneal tissue or decellularization can be accomplished using a variety of techniques. In one preferred embodiment, the cellular material of the cornea is removed by treatment with a chemical. The chemicals used to lyse and remove cells from the cornea include surfactants, such as, sodium tetradecyl sulfate (STS), acids, alkaline treatments, ionic detergents, such as sodium dodecyl sulfate (SDS), non-ionic detergents, such as, Triton X-100, and zwitterionic detergents. In some embodiments, the cellular material of the cornea is removed using an enzymatic treatment. Lipases, thermolysin, galactosidase, nucleases, trypsin, endonucleases and exonucleases are used to remove the cellular material from the cornea. In some embodiments, the cellular material of the cornea is removed using physical techniques. These physical techniques include methods used to lyse, kill, and remove cells from the matrix of a tissue through the use of temperature, force and pressure, and electrical disruption. Temperature methods are often used in a rapid freeze-thaw mechanism. Temperature methods conserve the physical structure of the ECM scaffold. Pressure decellularization involves the controlled use of hydrostatic pressure at high temperatures to avoid unmonitored ice crystal formation that could dam age the scaffold. Electrical disruption of the plasma membrane is another option to lyse the cellular material in the cornea.

In embodiments described herein, the method produces lenticules with reduced immunogenicity when implanted in the recipient's stromal bed. In some embodiments, the lenticule can be further treated to exhibit even lower immunoreactivity due to the degradation of immunogenic epitopes. This is an important step when using xenographic donations. For example, two non-human epitopes that may be present in xenograph tissue are N-Glycolylneuraminic acid (neu5GC) and Galactose-alpha-1,3-galactose (Alpha-Gal). These undesirable epitopes are present not only inside or on the surface of intrastomal cells; a small fraction of the epitopes can be embedded in the glyco-amino-glycans (GAGs), also known as mucopolysaccharides, that wrap around ECM collagen fibrils. In certain embodiments, the epitopes are removed by enzymatic treatments, such as kinase treatments, and additional washing. Alternatively, corneal tissue may be harvested from knockout transgenic pigs which lack epitopes, thus producing non-immunoreactive lenticules without requiring a degradation step. In some instances, it can also be preferable to remove epithelial and/or endothelial cell layers or residues from the lenticule prior to epitope neutralization. This can be accomplished by scraping, e.g., with a scapel, or by rubbing, e.g. with a cloth or abrasive material of suitable roughness.

In embodiments described herein, the methods of producing decellularized lenticules further comprise a sterilization step, which may be in conjunction with packaging and sealing. Sterilization can be accomplished using wet agents, gamma radiation, or electron beams. In one preferred embodiment, sterilization of the decellularized lenticule is performed using electron beams, as damage to the collagen scaffold is less likely to occur.

In yet another aspect of the invention, the posterior surface (opposite to the Bowman's membrane) is treated following excision, shaping and decellularization to make the surface more adherent to the stromal bed. For example, a crosslinking or adherence-enhancing agent can be applied, prior to sterilization and packaging. Alternatively, the crosslinking or adherence-enhancing agent can be applied by the clinician during the procedure before implantation.

In some embodiments, the preparation of the harvested, shaped and decellularized lenticule will include a step of marking the lenticule in such a way that the clinician can maintain the proper orientation of the lenticule during the reopening of the flap and laser adjustments. The marking can be done in a variety of ways, but in all instances will be invisible to the patient once the lenticule is in place. In some embodiments, the marking can be a micropscopic notch in the top anterior portion or the bottom anterior portion of the lenticule. In some embodiments, the marking can be a line or dot made with a dye placed at the top anterior or bottom anterior of the lenticule.

This invention and embodiments illustrating the method and materials used may be further understood by reference to the following exemplary protocol. Corneal tissue can be harvested from a porcine donor. The lenticule can be taken from an area within the donor corneal tissue as to maintain the high density of collagen type I fibrils or Bowman's membrane at the anterior surface of the lenticule and a less dense posterior surface. The target region of the donor cornea can be cut into a disc-shaped lenticule with a diameter of about 2-10 μm and a thickness of less than 200 μm. The lenticule can then be decellularized using techniques, such as chemical treatment, enzymatic treatment or physical techniques, to produce a lenticule which is 60-100% free of cellular material. If desired, the decellularized, shaped lenticule can be further treated to degrade immunogenic epitopes. The lenticule can further be washed and sterilized and, if desired, a crosslinking agent applied to the posterior surface of the lenticule. Finally, the top anterior surface of the lenticule can be marked with a notch to assist in lenticular orientation in the patient's stromal bed.

The invention claimed is:

1. A method for correcting an error in a subject's vision, comprising:
   implanting an intrastromal decellularized corneal lenticule within corneal stromal region of the subject's cornea such that a posterior surface of the implanted lenticule is positioned on an intrastromal bed of the subject's cornea, wherein the corneal lenticule includes a lenticular body derived from donor corneal tissue having an anterior surface that includes a Bowman's membrane from the donor corneal tissue and a posterior surface that is shaped to provide the lenticule with a desired shape for correcting an error in vision upon intrastromal implantation.

2. The method of claim 1, wherein said error in vision includes an abnormal refractive condition.

3. The method of claim 2, wherein said abnormal refractive condition includes any of myopia, hyperopia, presbyopia, and astigmatism.

4. The method of claim 1, wherein said lenticule has a maximum thickness less than 350 micrometers.

5. The method of claim 4, wherein the maximum thickness of the lenticule is less than 200 micrometers.

6. The method of claim 4, wherein the maximum thickness of the lenticule is less than 100 micrometers.

7. The method of claim 1, wherein the lenticule has a diameter in a range of about 0.5 mm to about 10 mm.

8. The method of claim 1, wherein the decellularized lenticule is 65%-95% cell-free.

9. The method of claim 1, wherein the donor corneal tissue is obtained from an allograft source.

10. The method of claim 1, wherein the donor corneal tissue is obtained from a xenograft source.

11. The method of claim 10, wherein the lenticule is substantially free of N-Glycolylneuraminic acid and Galactose-alpha-1,3-galactose.

12. The method of claim 1, wherein the lenticule has a disk-like shape.

13. The method of claim 1, wherein the posterior surface of the lenticule has been treated with a crosslinking agent to enhance its adherence to the intrastromal bed.

14. The method of claim 1, wherein the step of implanting the intrastromal decellularized corneal lenticule comprises:
   forming a hinged flap in a patient's cornea and folding the flap along its hinge to expose the intrastromal bed of the subject's cornea,
   placing the lenticule on the exposed intrastromal bed, and
   returning the flap to its unfolded position.

* * * * *